United States Patent [19]

Müller et al.

[11] Patent Number: 4,786,161

[45] Date of Patent: Nov. 22, 1988

[54] APPARATUS FOR EXAMINATION AND SURGERY OF THE ANTERIOR AND POSTERIOR PORTIONS OF THE EYE

[75] Inventors: Ortwin Müller, Aalen; Albrecht Vogel, Oberkochen; Ulrich Lemcke, Heidenheim; Gerhard Hanemann, Oberkochen; Fritz Strähle, Heubach-Lautern; Franz Muchel, Konigsbronn; Erich Blaha, Essingen, all of Fed. Rep. of Germany

[73] Assignee: Carl-Zeiss-Stiftung, Heidenheim, Fed. Rep. of Germany

[21] Appl. No.: 892,714

[22] Filed: Aug. 1, 1986

[30] Foreign Application Priority Data

Aug. 7, 1985 [DE] Fed. Rep. of Germany ....... 3528356

[51] Int. Cl.⁴ .............................................. A61B 3/10
[52] U.S. Cl. .................................... 351/205; 351/221
[58] Field of Search ....................... 351/205, 221, 214; 350/519, 520, 515, 523

[56] References Cited

U.S. PATENT DOCUMENTS 4,364,629 12/1982 Lang et al. ........................... 350/520
4,411,502 10/1983 Lang et al. ........................... 351/214
4,669,837 6/1987 Schirmer et al. ................... 351/205

Primary Examiner—Rodney B. Bovernick
Assistant Examiner—P. M. Dzierzynski
Attorney, Agent, or Firm—Stonebraker, Shepard & Stephens

[57] ABSTRACT

In an instrument for the examination and surgery of the eye, an ophthalmological objective is combined with an operation microscope whose main objective is combined with an optical system of variable back focus and focal length. Every plane of the eye lying between the cornea and the fundus is imaged by the instrument at an intermediate image plane. In this way, with a single instrument, the operator can carry out work on the cornea, the eye lens, the vitreous body, and the retina. Since the instrument provides the observer with a reflection-free image, contact of the eye to be operated upon with an optical auxiliary means which eliminates the refractive power is unnecessary.

2 Claims, 4 Drawing Sheets

APPARATUS FOR EXAMINATION AND SURGERY OF THE ANTERIOR AND POSTERIOR PORTIONS OF THE EYE

BACKGROUND OF THE INVENTION

This invention relates to apparatus for the examination and surgery of both the anterior portions and the posterior portions of the eye.

For examination and operative therapy in the anterior portion of the eye, there have been available for a long time operation microscopes providing stereoscopic observation and which permit paraxial illumination with the instrument and oblique illumination by means of fiber optics or by slit illumination, and which are equipped with a pancratic variation of magnification as well as with connecting means for a co-worker's microscope and for documentary apparatus.

An observation microscope for several observers which has a pancratic system in the observation ray path is described in Fed. Rep. Germany patent No. 29 49 428 and in the corresponding U.S. Pat. No. 4,341,435 of Lang et al., granted July 27, 1982. An optical system of variable back focus and focal length which can be combined with the main objective of an operation microscope is disclosed in Fed. Rep. Germany Offenlegungsschrift (published but unexamined patent application) No. 32 02 075 A1 and in the corresponding European patent No. 0 085 308 and U.S. Pat. No. 4,525,042 of Muchel, granted June 25, 1985. The illumination ray path in an operation microscope is illustrated on page 222 of the English-language book "Handbook of Ophthalmic Optics," published 1983 by the Carl Zeiss firm of Oberkochen, West Germany, and on page 223 of the German-language edition of this book, published 1977 by the Zeiss firm under the title "Handbuch für Augenoptik."

For the examination of the posterior region or fundus of the eye, ophthalmoscopes are known which make it possible, by direct or indirect observation, to illuminate and observe the retina of the eye, through the pupil, by means of mirrors or prisms. Such ophthalmoscopes are known, for instance, from pages 216 and 217 of the English-language edition of the above-mentioned Handbook.

SUMMARY OF THE INVENTION p The object of the present invention is to provide an instrument with which microscopic examination and microsurgery can be carried out on both the anterior and posterior portions of the eye. The anterior portions of the eye comprise the cornea, iris, and lens. In operative therapy on the posterior portions of the eye, so-called vitrectomy, the vitreous body and the retina are concerned.

This object is achieved, in accordance with the invention, by providing, in front of the main objective of an operation microscope, an ophthalmoscopic objective which images in an intermediate image plane each plane of the eye lying between the cornea and the fundus. The back focus and the focal length, as well as the magnification of the entire optical system of the apparatus, are infinitely variable. Also, there is provided a system for the lateral interchange of the pupils for simultaneous image inversion in the stereoscopic ray path, as well as a system for eliminating the reflections occurring in the illuminating ray path.

The combined use of the apparatus as an operation microscope for the anterior portion of the eye and as a stereoscopic ophthalmoscope for the posterior portion of the eye is assured by an achromatic aspherical ophthalmoscope objective having a focal length of $f=25.7$ mm, arranged in front of the main objective of an operation microscope. The ophthalmoscope objective preferably can be positioned at a variable distance from the eye of the patient. The ophthalmoscope objective provides an intermediale image of the object, which intermediate image is observed through the operation microscope.

For observation of the fundus, the ophthalmoscope objective is positioned at the distance of its focal length f from the cornea of the eye of the patient. The fundus is imaged into the intermediate image plane by the refractive power of the system consisting of the eye plus the ophthalmoscope objective. Regarding illumination, the exit pupil of the illuminating apparatus is focused in the pupil of the eye to be examined as is customary in the use of ophthalmoscopes.

For examination of the anterior portions or outer media of the eye, the ophthalmoscope is positioned at a distance of 2f from the cornea of the eye of the patient. The object is imaged by the ophthalmoscope objective with image inversion in the intermediate image plane. The ophthalmoscopic illumination then acts at the place of the object as a paraxial microscope illumination, and homogeneously brightens a field of about 15 mm in diameter.

By the combination of the main objective of the operation microscope with an optical system of variable back focus and focal length, such as is known in principle from the above mentioned U.S. Pat. No. 4,525,042 of Muchel and the corresponding German and European patent documents, the result can be obtained that the microscope has not only pancratic variation of magnification but also continuous objective focusing by which the fixed focal length of the main objective (e.g., $f=225$ mm) can be infinitely varied between $f=150$ mm and $f=400$ mm. This has the desirable result that the operating ophthalmologist can keep the operation microscope fixed in one position relative to the patient's eye and, from this fixed position, can bring into proper focus simply by operation of the objective focusing control, the entire region from the retina up to the posterior lens vertex. This is of particular importance for operation on the vitreous body (vitrectomy). Up to a myopia of $-30$ diopters of the eye of the patient, when using an ophthalmoscope objective with a refractive power of 40 diopters, a continuous change in focal length of about 85 mm is necessary in order to focus over all of said range. By suitable electronic controls and drives, the result is obtained that the changing of the linear magnification, caused by the changing of the back focus of the lens focusing, is eliminated by means of the pancratic variations of magnification. fication.

In this case, different linear magnifications can be selected. Similarly, the functional connection between objective focusing and pancratic focusing can be interrupted at any time, so that different planes in the region of the vitreous body can be observed with different linear magnification.

For the elimination of reflections, there is provided within the illuminating ray path, near the field stop, at least one glass plate which can be finely adjusted in three coordinates in space. Opaque pairs of points, which take stereoscopic observation into account, are applied to this plate. The pairs of points are so arranged that they eliminate the rays coming from the source of light which are reflected by the three surfaces of the ophthalmoscope objective into the two observation pupils and superimpose an image of the source of light on the image of the fundus.

By this optimalizing of the ray guidance which is necessary for the elimination of reflections, the illuminating optics is imparted the quality of a focusing optics in which, by increasing the illumination aperture, the shadow projection coming from the pairs of points is reduced to a minimum, so that the ophthalmoscope imaging does not have any loss of information.

One suitable embodiment of the invention provides means for coupling therapeutic laser radiation into the illuminating ray path. In this connection, the real intermediate image plane is shifted within the illumination ray path to the place at which the filament of the illuminating lamp is located during ordinary use of the instrument as an operation microscope or as a stereo ophthalmoscope. Within this plane there also lies the exit pupil of the laser radiation which is to be focused in the object and focal planes of the microscope for therapeutic purposes. The instrument is so constructed that by the placing on of a prepared double collector with incandescent bulb, a real image of the filament of the lamp is superimposed on the said intermediate image plane of the laser-light coupling.

In order to compensate for ametropias when giving laser treatment to the eyes of a patient, it is advisable, in accordance with refractometer principles, to provide in the illumination and laser ray paths an optical shift member which is moved synchronously with the internal focusing of the microscope, so that the intermediate image plane and the laser focus plane are always identical.

The advantages resulting from the present invention include, especially, the fact that the user has a single instrument for work on the cornea, the eye lens, or the retina, which instrument will provide, for all of these locations of work, a stereoscopic, erect, and laterally correct image, with a fully illuminated field of view. Another important advantage is that, due to the reflection-free observation of an ophthalmoscopic intermediate image, it is unnecessary for the eye which is to be operated upon to be contacted by an auxiliary optical means, such as a contact lens, in order to eliminate the refractive power of the cornea.

BRIEF DESCRIPTION OF THE DRAWINGS

In the accompanying drawings, which illustrate schematically a preferred embodiment of the invention.

DESCRIPTION OF THE PREFERRED EMBODIMENT

Figure 1:
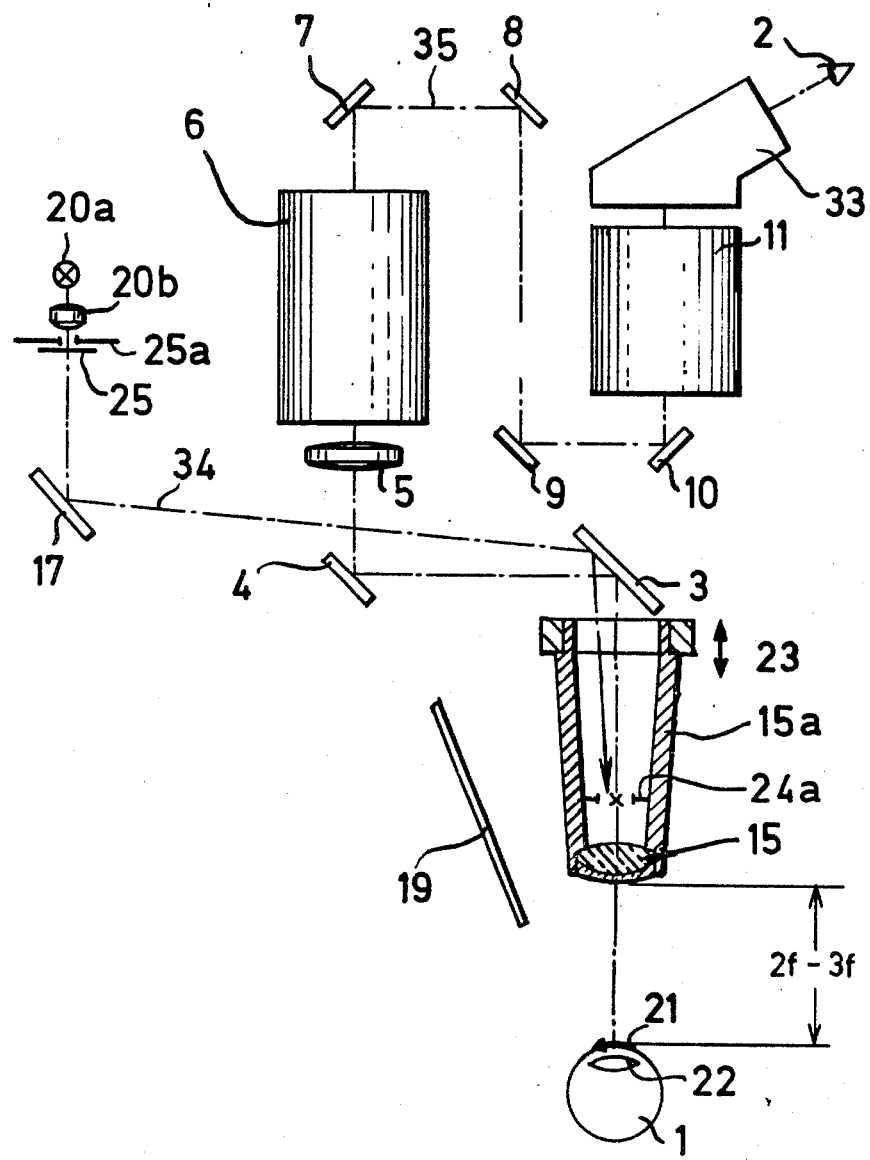
FIG. 1 is a diagram showing the apparatus of the invention in the working position for use as a microscope.

Referring first to FIG. 1, there is shown here a schematic diagram of the apparatus of the invention in the working position of an operation microscope, for examination of or surgery upon the external media of the eye.

The eye of the patient is shown at 1, and the eye of the observer at 2. The observation ray path extends from the eye 1 of the patient, via the deflection elements 3 and 4, to the main objective 5 of the operation microscope, then through a conventional known optical system 6 of variable back focus and focal length, and along the ray path indicated at 35, via the deflecting elements 7, 8, 9, and 10, to a prism arrangement 11 for the interchange of the pupils, and thence to the conventional binocular viewing tube 33 of the operation microscope, and to the two eyes of the observer using the instrument. Only one eye of the observer is shown at 2, the second being hidden behind the one shown, in this direction of viewing, as well understood by those familiar with binocular viewing devices.

In the observation ray path, between the eye 1 of the patient and the reflecting element 3, there is placed the ophthalmoscope objective 15. This is an achromatic aspherical ophthalmoscopic objective having a focal length of $f = 25.7$ mm. When the device is used for examining the external media of the eye (the mode illustrated in FIG. 1) it is positioned so that the ophthalmoscope objective 15 is spaced a distance of from 2f to 3f from the eye, as indicated by the numerical notation in FIG. 1. At the distance of 2f from the eye, it is possible, with slight pancratic magnification and thus with large depth of field, to view in its entirety the complete region from the retina up to the iris of the patient, even without actuation of the internal focusing mechanism.

To provide illumination of the object being viewed, there is a light source 20a which projects light through a condenser lens 20b, along an illumination ray path 34. It is reflected by the reflector element 17 to the previously mentioned reflector element 3, where the illuminating ray is again reflected to the ophthalmoscope objective 15 and passes through this objective to the object being examined, i.e., the patient's eye 1.

In addition to this illumination ray 34 from the source 20a, supplemental fiber-optical illumination shown schematically at 19 may also be provided.

With the optical system 6, the operation microscope, in addition to a pancratic variation in magnification of an expansion ratio of 6:1, also has a continuous objective focusing by means of which the fixed focal length ($f = 225$ mm) of the main objective 5 can be infinitely varied between the limits of 150 mm and 400 mm.

Objective focusing and pancratic magnification are advantageously employed when an instrument in accordance with the invention is to be used merely for observation and therapy of the external media. In such case, the instrument is first positioned roughly so that the vertex distance from the lens 15 to the eye of the patient is 2f to 3f which, as above mentioned, is the distance schematically shown in FIG. 1. This is done by the mechanical means present, namely, by movement of the arm of the microscope stand, or by operating a conventional positioning motor (not shown) by means of a conventional external focusing control member (also not shown), in which connection the entire microscope is moved. The actual fine focusing necessary as a function of the object plane selected is then effected during the operation by the above-mentioned objective or internal focusing on the intermediate image produced within the instrument by the ophthalmoscope objective. During this focusing, the position of the instrument and thus also the position of the microscope eyepiece remains unchanged. The relatively large vertex distance from the instrument to the eye of the patient (two or three times the focal length of the ophthalmascope objective 15) gives sufficient room for manipulation to perform surgical acts on the outer eye. The ophthalmoscopic paraxial illumination is then advisedly supplemented or replaced by external oblique illumination, as for example by means of the fiber optics illuminating means 19.

Figure 2:
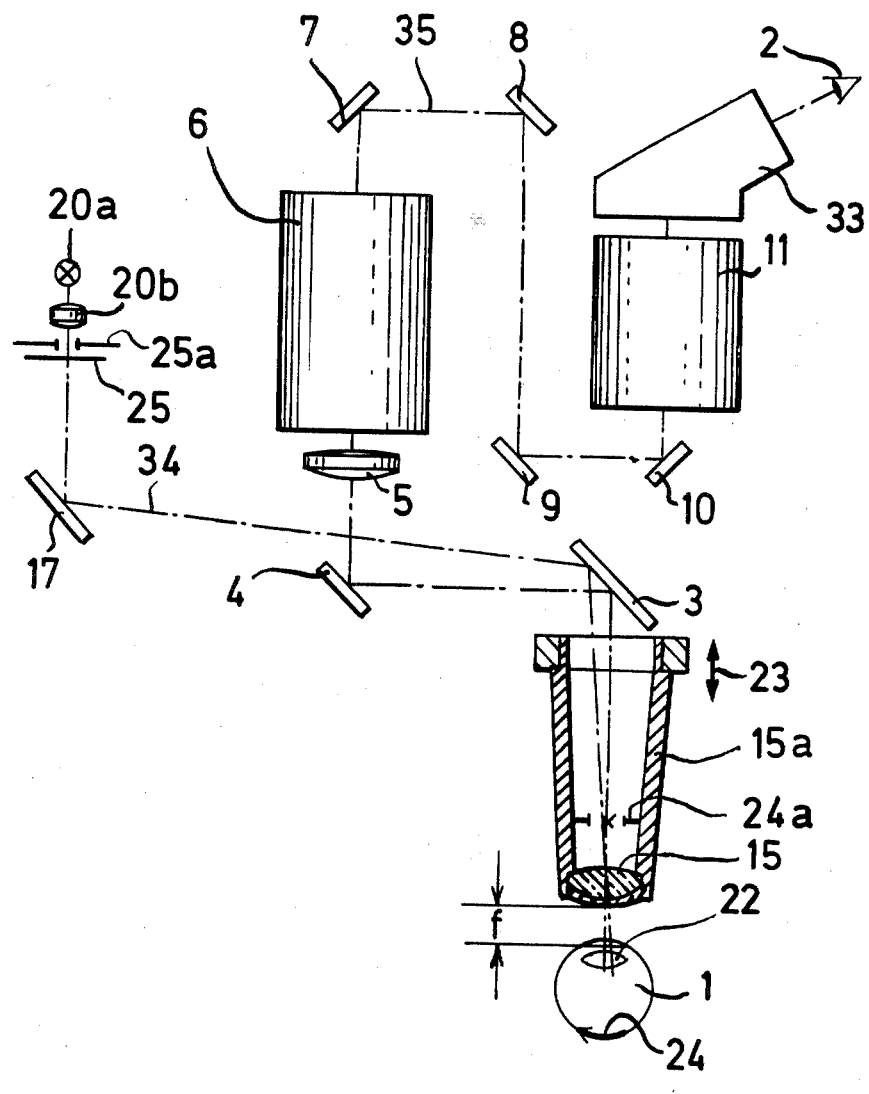
FIG. 2 is a diagram showing the apparatus in the working position for use as an ophthalmoscope.

In FIG. 2 the apparatus is placed so that the ophthalmoscope objective 15 is spaced from the eye 1 of the patient by the closer distance f, rather than 2f to 3f as in FIG. 1. This closer spacing is the working range used when the examination or surgery is in the region from the rear surface of the eye lens 22 to the fundus 24.

In order to obtain a sufficiently large stereoscopic base, the illumination is effected in the case of the stereoscopic ophthalmoscope by means of an elliptical mirror. By tilting the axis of the illuminating ray path 34 with respect to the axis of the observation ray path 35, the reflections by the eye lens 22 are eliminated. The reflections produced on the cornea are no longer disturbingly apparent, in view of the fact that an achromatized ophthalmoscope objective is used. Mirror and cornea are optically conjugated with each other. Injurious widening of the ghost reflection of the cornea is avoided by the achromatism.

In order to eliminate the reflections coming from the surface of the ophthalmoscope objective, a parallelsided plate 25 is introduced close to the field stop 25a and a decentralized pair of points is arranged on this plate. This pair of points is split into one pair of points for the virtual reflection and one pair of points for the two real reflections. A reflection-free imaging without disturbing visibility of the pairs of black points is obtained in the manner that the illuminating optical system is so changed that a higher illumination aperture becomes effective. The ophthalmoscope objective 15 focuses the fundus 24 at the intermediate image plane 24a.

The ophthalmoscope objective 15 is carried by a lens tube or mount 15a which may be moved in the direction of the double-headed arrow 23, toward and away from the patient's eye 1.

Figure 3:
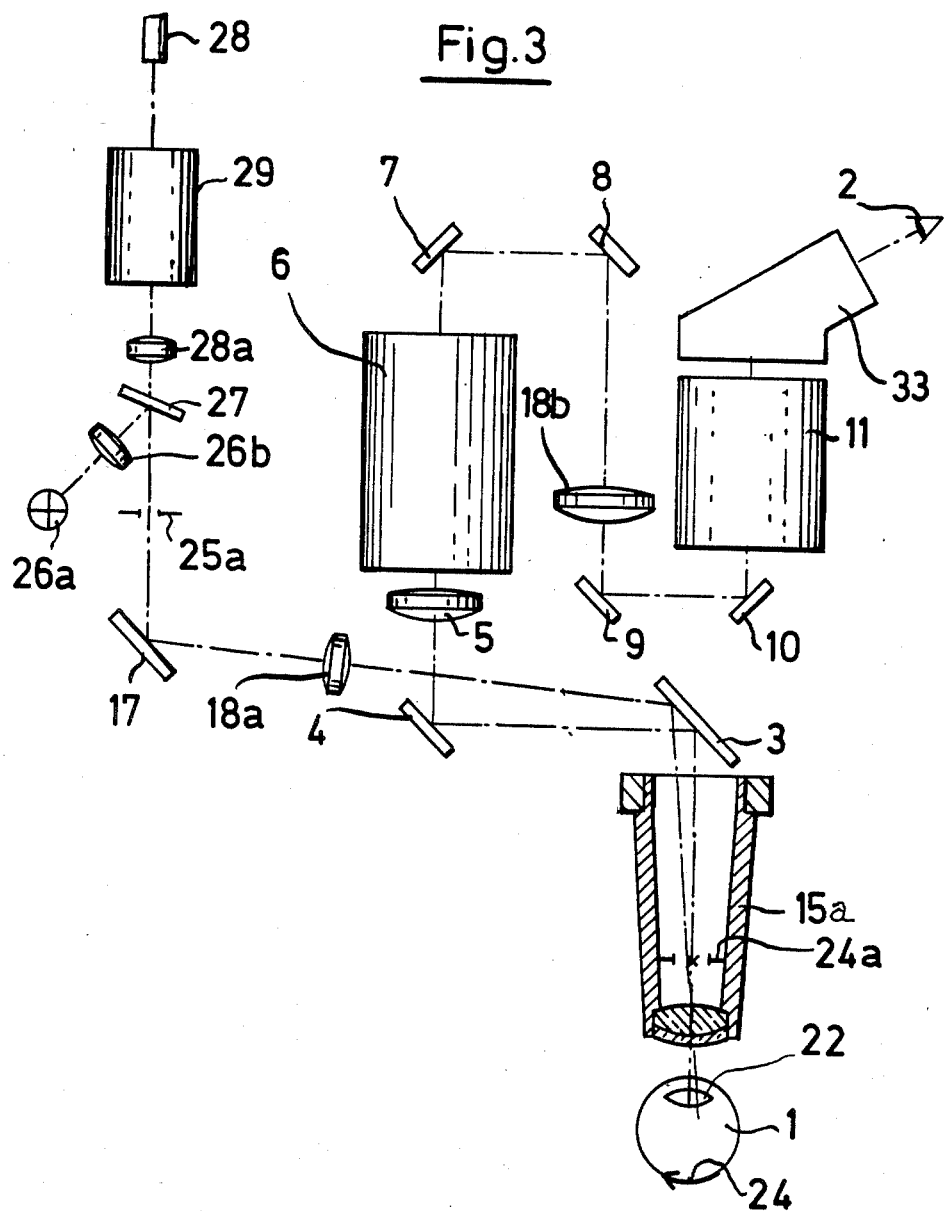
FIG. 3 is a view similar to FIG. 2 with the addition of laser coupling means.

FIG. 3 illustrates the coupling of a laser into the stereoscopic operation ophthalmoscope. A laser 28 produces a laser beam which passes through an optical displacement member 29 and through a converging lens 28a to a semi-transparent mirror 27. The laser beam passes through this mirror 27 and here passes into the illumination beam which originates at the light source 26a. A real image of the filament of the lamp 26a is superimposed on the laser coupling via the double collector lens 26b. From this mirror 27 onward, the coupled beams (laser beam plus illuminating ray beam) pass through the field stop 25a and follow the same path (reflecting elements 17, 3 and objective 15) to the eye of the patient as in FIGS. 1 and 2.

For compensating for ametropia of the eye of the patient, the illuminating and laser beam path is preferably provided with an adjustable compensating slide member schematically shown at 18a, and the observation beam path is provided with a corresponding adjustable compensating slide member schematically shown at 18b. These two slide members are operatively interconnected by conventional connecting means for synchronous operation with the microscope internal focusing, so that the intermediate image plane and the laser focus plane are always identical.

Figure 4:
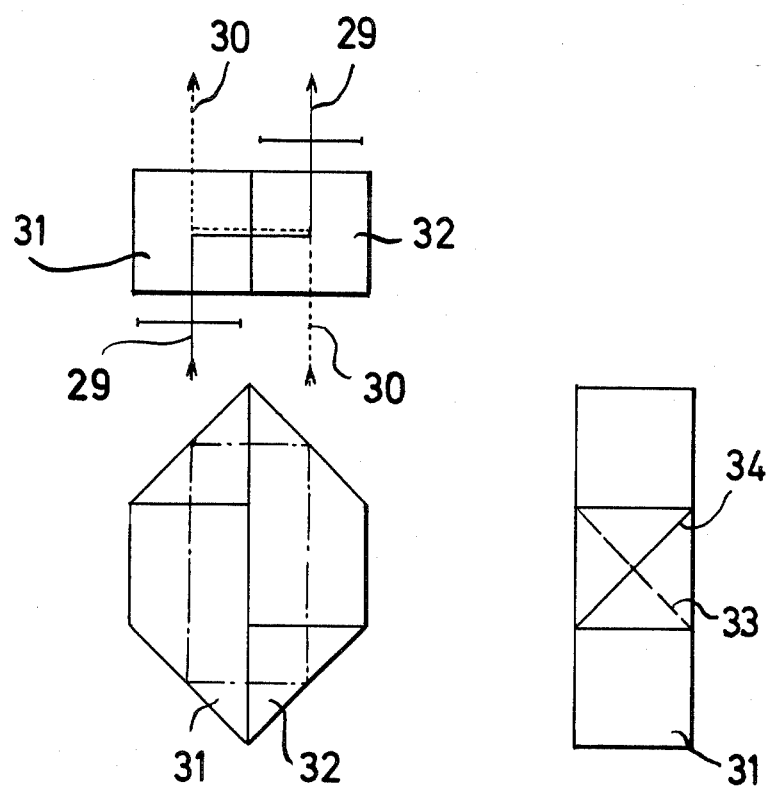
FIG. 4 shows a prism arrangement for lateral interchange of the pupils.

FIG. 4 illustrates a prism system which may be used as the pupil exchanger indicated in general at 11 in FIGS. 1–3. In the arrangement of the prisms shown, the two stereoscopic ray paths 29 and 30 are interchanged with each other, with simultaneous turning of the image positions by 180 degrees, while maintaining constant the pupil spacing and the position thereof. This pupil interchange with simultaneous image inversion is necessary for observing the ophthalmoscopic intermediate image with the operation microscope.

The prism arrangement designated 31 and 32 consists, in each case, of four identical Porro prisms whose hypotenuses 33, 34 have fully mirrored (fully reflecting) action toward both sides. With this prism arrangement, there is obtained a small structural height with little loss in light, but on the other hand the optical wavelengths do not remain constant. If the optical wavelengths are to remain constant, a more expensive arrangement with rotatable prisms should be used.

For the optical system 6 of the operation microscope, there can be provided electronic controls and drives which see to it that the change in the linear magnification which a change in back focus of the objective focusing produces is eliminated by means of the pancratic variation of magnification. In this connection, different linear magnifications can be preselected. The functional connection between objective focusing and pancratic function can be eliminated at any time, so that different planes in the region of the vitreous body of the eye can be observed with variable linear magnification. The operation microscope can be positioned by electric motor means in three coordinates in space (x-y coupling, z-focusing coupling), the control commands being actuable, for instance, by the operation of a foot pedal.

What is claimed is:

1. Apparatus for examination and surgery of the anterior and posterior portions of the eye, said apparatus comprising an operation microscope having a main objective (5), an opthalmoscopic objective (15) located in front of said main objective and positioned and dimensioned to produce, on an intermediate image plane (24a) lying between said two objectives, an image of each plane of the eye lying between the cornea (21) and the fundus (24) thereof, said apparatus having an optical system in which back focus and focal length and magnification are infinitely variable, said apparatus further comprising an optical system (11) for lateral interchange of pupils with simultaneous image inversion in a stereoscopic ray path, and means for eliminating reflections occurring in an illumination ray path, wherein said apparatus includes means producing an illumination ray path, and a field stop (25a) in said path, and wherein said apparatus includes means producing an illumination ray path, and a field stop (25a) in said path, and wherein said means for eliminating reflections comprises at least one glass plate (25) located in said illuminating ray path close to said field stop, said glass plate being mounted for fine adjustment in three coordinate directions and having an opaque pair of points on said plate.

2. Apparatus for examination and surgery of the anterior and posterior portions of the eye, said apparatus comprising an operation microscope having a main objective (5), an opthalmoscopic objective (15) located in front of said main objective and positioned and dimensioned to produce, on an intermediate image plane (24a) lying between said two objectives, an image of each plane of the eye lying between the cornea (21) and the fundus (24) thereof, said apparatus having an optical system in which back focus and focal length and magnification are infinitely variable, said apparatus further comprising an optical system (11) for lateral interchange of pupils with simultaneous image inversion in a stereoscopic ray path, and means for eliminating reflections occurring in an illumination ray path, said apparatus further comprising means for coupling a beam of therapeutic laser radiation into an intermediate image plans of said illumination ray path, and further comprising an optical slide member in said illumination ray path containing said laser radiation, and an optical slide member in an observation ray path extending through said main objective (5) and said ophthalmoscopic objective (15), said slide members being associated for synchronous operation and serving to compensate for ametrophia in an eye of a patient.

* * * * *